ized Patent [19]

Green et al.

[11] 4,377,340
[45] Mar. 22, 1983

[54] METHOD AND APPARATUS FOR DETECTING PARTICLES ON A MATERIAL

[75] Inventors: Gary P. Green, Marlborough; Charly D. Allemand, Newtonville; David L. Brewer, Stow; Hitoshi Iida, Bedford; Mario A. Maldari, Stow, all of Mass.

[73] Assignee: Hamamatsu Systems, Inc., Waltham, Mass.

[21] Appl. No.: 200,566

[22] Filed: Oct. 24, 1980

[51] Int. Cl.³ ............................................. G01N 21/47
[52] U.S. Cl. .................................... 356/237; 250/562; 250/572; 358/106
[58] Field of Search ............... 356/336, 338, 342, 237, 356/430, 431, 446; 250/562, 572; 358/106

[56] References Cited

PUBLICATIONS

Grosewald et al., "Automatic Detection of Defects on Wafers" IBM Tech.-Disclo. Bull., vol. 21, No. 6, pp. 2336–2337, 11/78.
Adler et al., "Detecting and Analyzing Wafer Defects", IBM Tech. Disclo. Bull., vol. 12, No. 10, pp. 1672–1673, 3/70.

Primary Examiner—John K. Corbin
Assistant Examiner—Matthew W. Koren
Attorney, Agent, or Firm—Irving M. Kriegsman

[57] ABSTRACT

A method and apparatus for detecting and measuring the number and sizes of impurities on the surface of a material, such as a semiconductor wafer, wherein high intensity collimated light is directed onto the surface, in the absence of any extraneous light, through a collimating mirror, and employing a point source, whereat the particles will scatter the light, and wherein the surface is viewed by a highly light sensitive TV camera which picks up the scattered light and displays same on a viewing screen. The intensity of scattered light will indicate the size of the particles when compared with a calibrated model. Advantageously, a broad range of light waves is employed and thus enables a range of sizes of particles to be detected by the light scattered thereby. Also, advantageously, with the use of ordinarily available equipment, the system can inspect wafer surfaces for particles having sizes as small as 0.3 microns. The system also enables detection and identification of moving particles as distinguished from stationary particles.

16 Claims, 6 Drawing Figures

METHOD AND APPARATUS FOR DETECTING PARTICLES ON A MATERIAL

BACKGROUND OF THE INVENTION

This invention relates to a method and apparatus for the detection, identification and measuring of the number and sizes of particles on a material, such as the surface of a semiconductor wafer.

In the prior art, there have been a variety of ways in which to detect, and measure the number and sizes of particles on a semiconductor wafer, for the purpose of rejecting those wafers which had on the surface, one or more particles of undesired sizes, e.g. from 1 to 20 microns, or for those having on the surface an excessive number of such particles. One of the most prevalent methods employes the human operator using a light field/dark field microscope. Using the human eye, the human operator would actually count the number of particles and also identify the size of the particles, such as those between 1 to 20 microns, and then remove those wafers which had an excessive number of particles or those having particles of a certain size. This method is without doubt highly inaccurate, and very expensive both in terms of wages for the human operator, and in terms of the number of rejects both after the inspection and after production of the chips (when the erroneously passed wafer would be found to have an electrical defect, e.g. short circuits, because of the presence of contaminant particles).

It is well known that contaminant particles on a semiconductor surface can cause open circuits, short circuits and other defects in the integrated circuitry placed thereon or manufactured thereof. Integrated circuits can have circuitry as small as 2.5 microns or less in more advanced technology. For the sake of economy, and since there are so many steps for the manufacture of integrated circuits after inspection of the raw wafer surface, the contaminated wafers must be removed from the production line before the numerous steps of manufacture are started. In some cases, wafers having an excessive number of particles about 1 micron in size must be removed, although at the present state of the art, the particles can be slightly larger in many cases and still be acceptable for circuitry preparation.

Another method is the use of a helium/neon laser to scan the wafer surface and using a photomultiplier to detect the reflected beams. The particles on the wafer surface will reflect light from the laser beam unto a photomultiplier with the number of pulses received by the photomultiplier being the particle count, and the intensity of the pulses being the indication of the size of the particles. This method, however, has not been fully exploited and developed, and has such defects as requirement of an expensive set of optical devices to form the appropriate laser beam and to scan same across the wafer surface, and requirement of mechanical masks to direct the beam. Also, the scanning, whether done by a set of optical devices or otherwise, is slow, requiring about 2 to 4 seconds for a 3 inch wafer. The photomultiplier detector also can scan only one spot at a time as the laser spot is removed across the wafer surface. Thus, there is an inherent problem with the use of laser beams, namely, that only one spot at a time is detected. The laser beam is not scanned at a very fast speed across the wafer surface. Also, disadvantageously, the photomultiplier cannot detect which particle is moving and which is stationary since the light used to illuminate the particles is the narrow beam of the laser and the moving particles which are hit by the laser beam on one line scan may be missed on the next line scan. Thus, there is no way in which an accurate map could be made of the moving particle, and hence, such moving particle may be viewed by the photomultiplier as being a stationary particle. There is no way that the laser beam can be scanned across the wafer and down the wafer at the same speed as a vidicon electron gun which scans a television camera. A further and more practical disadvantage to use of a laser system is the expensive auxiliary safety equipment which must be employed in conformance with governmental standards and regulations for the use of lasers.

There is an urgent need, for example, in the semiconductor industry, as well as other industries, for a simple and inexpensive method and apparatus for the detection, identification and measurement of the number and sizes of particles on the surface of or in a material, such as a semiconductor wafer, which also can be operated by an unskilled operator. The particles to be detected are from 0.3 microns and above. Particles larger than 20 microns will usually be priorly removed by ordinary cleaning methods.

SUMMARY OF THE INVENTION

Accordingly, an object of the invention is to eliminate the aforementioned and other deficiencies and disadvantages of the prior art.

Other objects of the invention are to provide a relatively inexpensive and simple procedure for the detection, identification and measurement of the number and sizes of contaminant particles having sizes smaller than 20 microns, and more particularly, those particles having sizes less than 1 micron, such as 0.3 micron and larger, employing readily available sub-components.

Other objects are to employ a detection system which does not rely upon human eye judgment, and which does not use a laser source.

The foregoing and other objects of the invention are attained by the inventive method and apparatus for detection, identification, and measurement of the number and sizes of contaminant particles on the surface of or in a material, such as for example, a semiconductor wafer. An intense light beam having a broad spectrum of wave lengths, is collimated by suitable lenses, pinhole device and mirror, and then directed onto the surface of the wafer being inspected. The collimated light is then reflected back toward the source along substantially the same light path from the wafer surface. The particles will scatter the light and according to the size of the particles, the scatter envelope will be of proportional size in the forward and backward and "Y" directions. A highly light sensitive TV camera is pointed at the surface and focused by suitable lens to a selected portion of the surface or the entire surface, to detect the envelopes of scattered light. By having priorly calibrated the scatter light intensity to the size of the particle, the camera and associated processor can, by simple viewing, determine the presence, number and sizes of the particles. The housing for the equipment should be substantially light reflectionless, such as coated with black material. Also, the other devices and equipment within the housing should also be substantially reflectionless. An adjustable iris may be disposed between the collimating mirror and the wafer surface in order to precisely determine the area of contact of the light beam on the wafer surface. Alternatively, a mask may be used on the lens which is used to focus the light beam from the light source into a small source. The mask would enable light to only impinge on selected areas of the surface of the wafer. Using this invention, it was discovered that particles of about 0.5 microns could be repeatedly detected, identified and measured. It was also found that particles of about 0.3 microns were detected, although the accuracy of measurement was not entirely precise. It may be possible to detect particles of about 0.1 microns, but the measurement thereof could not be confirmed. Thus, advantageously, the invention enables the unskilled operator to detect, measure and identify the number and sizes of contaminant particles on the surface of a semiconductor wafer surface, for example.

A feature of the invention is the use of a collimated broad spectrum light source to illuminate a semiconductor or other material surface with the light being reflected back to the source from the surface without causing extraneous light to emanate, and the use of a light sensitive vidicon and processor to detect, identify count and measure the number and sizes of envelopes of light scattered by the particles in response to the collimated light impinging thereon.

Another feature is the use of collimated light to illuminate the semiconductor surface wherein light is scattered by the contaminant particles thereon, and which scattered light is detected by the light sensitive TV camera.

A further feature is the use of an adjustable iris disposed between the collimating mirror and the semiconductor surface to define the area of contact of the collimated light on the surface and to prevent reflections off of the wafer's edges.

Another feature is the use of a mirror and iris to direct a collimated light beam to a specified area of the surface of the wafer, and to eliminate diffusion and reflection of light from the edges of the wafer.

A further feature is use of a mask on a lens near the light source such that the mask is imaged on the wafer, and the movement of the wafer so that preselected portions of the wafer can be illuminated by collimated light and viewed by the vidicon camera at different times for the detection, counting, identification and measurement of the number and sizes of particles in that section illuminated, until substantially the entire wafer is processed for inspection.

Another feature is the use of a housing which is substantially light reflection-free and substantially free of any extraneous light.

Another feature is the use of a light source having a broad spectrum of wave lengths, wherein the particles of different sizes optimally scatter light of different wave lengths.

A further feature is the use of a variable focal length lens on the camera to view with a greater magnification a small portion of the wafer being inspected to thereby enable detection of smaller sized particles, such as about 0.5 microns in size or smaller.

Another feature is the adjustment of the angle at which the camera is directed to the plane of the surface of the wafer, being optimally about up to 17 degrees.

A still further feature is the substantially instant display on a viewing screen of the entire wafer surface and the location, number and sizes of the contaminant particles thereon.

Another feature is the rapid scanning of the entire wafer surface, such as about 33 milliseconds for a 3 inch wafer, and the obtaining thereby of the required detection of the particles.

A further feature is the detection of moving particles and the distinguishing of such moving particles from stationary particles.

DETAILED DESCRIPTION OF THE PREFERRED EMBODIMENTS

Figure 1:
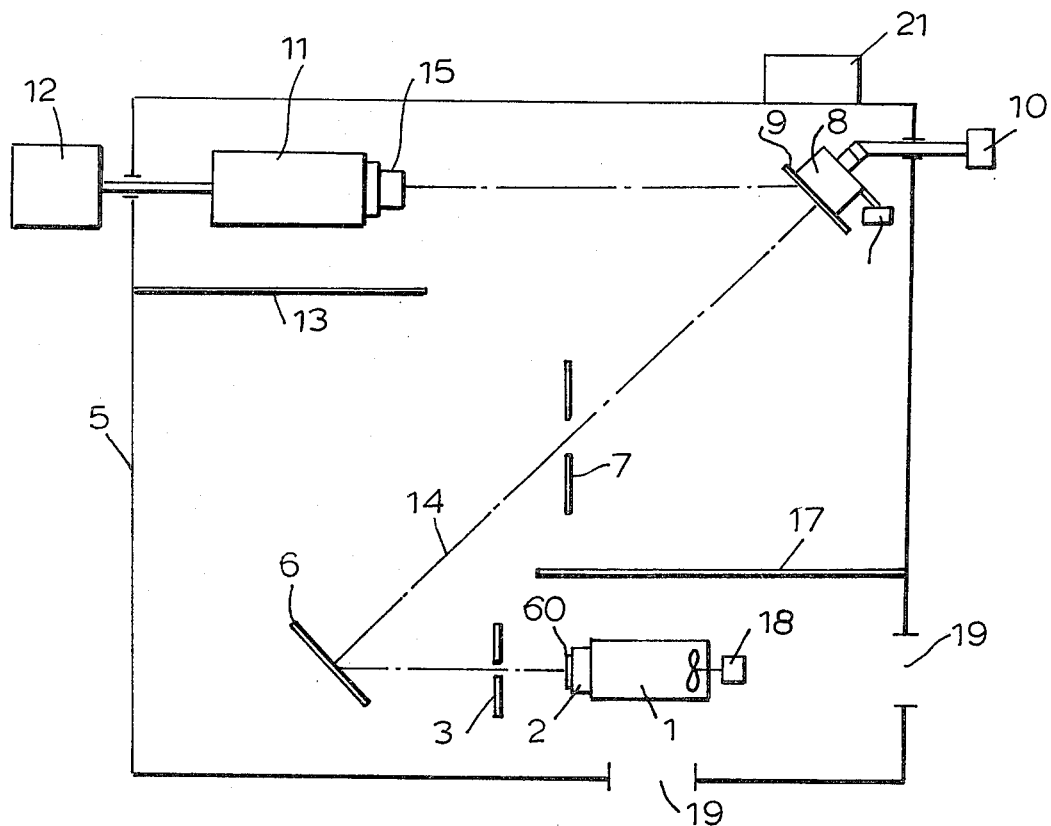
FIG. 1 depicts a diagram of an illustrative embodiment of the invention.
Figure 6:
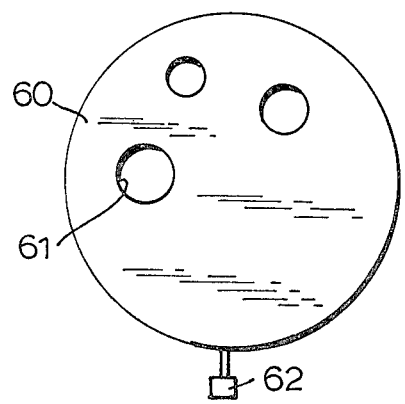
FIG. 6 depicts a mask which may be used on the lens previous to the light beam being focused to a point source, and which mask is to define the area of illumination on the wafer surface.

Turning now to FIG. 1, there is depicted an illustrative embodiment system for detecting, measuring, identifying and counting the number and sizes of contaminant particles on a semiconductor wafer surface. In a housing 5, which preferably has interior walls of black material to prevent unwanted light reflections and scattering, there are placed a highly light sensitive TV camera 11, lens 15, an iris 7, a collimating mirror 6, and a vacuum chuck 8 for holding a wafer to be inspected. The iris 7 which may be suitably coated with black or other light suppressing color or material, may be suitably adjusted to direct the light to the area of the wafer surface desired. For example, the iris 7 can cut off any light to the edges, and thus prevent light scatter or reflections from such edges. Another way of focusing the collimated light on a specific part of the water surface is to use a mask, such as of black non-flammable material, which can be placed on the lens 2 located in front of the light source 1. Such a mask 60 is shown in FIG. 6 having a plurality of different holes or patterns 61. The mask also may be connected to a means 62 for moving the mask. Thus, when a specific area of the wafer surface is desired to be inspected, a mask 60 or an iris 7 may be used to restrict the collimated light 14 to that area of the wafer surface. The camera 11 may be focused by the lens 15 then to see only that area at a greater magnification. In this manner, the resolution of the smaller particles may be enhanced.

The holder 8 is connected to vacuum pump 10 via a hose. The vacuum pump 10 reduces the pressure at the holder surface so that the wafer may be held by the vacuum without any touching of the surface to be inspected. To place the wafer onto the holder, a vacuum operated pick-up device may be used to pick up the back of the wafer or chip, and then the wafer is moved to the holder 8 and the vacuum of the holder 8 then takes hold of the back of the wafer. In this manner, no human hands will touch the wafer surface and further contaminate same. The light beam 14 is generated by a light source 1, which may be a 150 watt Xenon arc lamp, and is focused by lens 2 through a pin hole device 3, and then collimated by mirror 6 and directed through adjustable iris 7, to be confined to a specified area of the wafer 9 surface.

As shown in FIG. 1, there is provided between the camera 11 and the light path including the collimating mirror 6, a wall 13 which is also coated of non-reflection material such as black material, and works to isolate the camera 11 from the light 14 being directed at the target or wafer 9. The camera 11 is light sensitive and thus can pick up any scattered or extraneous light within the housing. This extraneous light may interfere with the sensitive operation of the camera in picking up the light scattered by the particles on the surface of the wafer. The accuracy of the pickup of the camera will be adversely affected by the presence of any extraneous light. Thus, the inside of the housing and wall 13 should be substantially light reflectionless and scatterless. Also the housing is substantially sealed in a way to exclude extraneous outside light. Similarly, another wall or baffle 17 is provided between the light source 1 and the target 9 for similar reasons. Also, this wall isolates the heat from the light source 1 from affecting the target 9 and the light path 14 and provides a baffle to direct air past the source 1.

The embodiment may also provide a laminar flow apparatus 21, which will send a clean laminar flow of air about the wafer 9, and then around the wall 17, and about the light source 1. In this manner, the area about the wafer 9 surface may be kept substantially clean of other particles, and the heat from the light source 1 may be dissipated out of opening 19 cut into the walls of the housing 5. In the event the light source is built outside of the housing, a fan 18 may be used to cool the light source.

Figure 2:
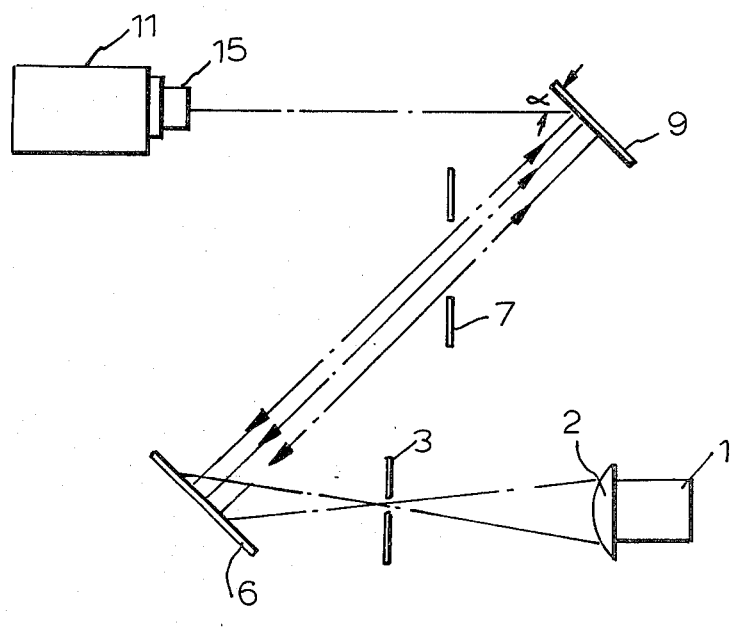
FIG. 2 depicts the light path in the embodiment of FIG. 1.

Turning to FIG. 2, light source 1 generates a light beam which is focused by lens 2 to a small source whereat is provided a pin hole device 3 for excluding extraneous light except for the small source. The pin hole device 3 should be of black material to absorb extraneous light. The light beam 14 is directed onto collimating mirror 6, which then collimates the light 14 and directs same as substantially parallel beams onto the surface of the wafer 9. An adjustable iris 7 (See FIG. 1) is disposed between the mirror 6 and wafer 9, and is used to define the light beam on a preselected area on the wafer surface. The light beam 14 is collimated to enable substantially unidirectionality and parallelity of the light and thus minimize thereby any unwanted light reflections and scattering. The light beam 14 after hitting the wafer surface will be reflected back along substantially the same beam path. In this manner, substantially very little or no extraneous light is exposed to the camera 11, and substantially only the light scattered by the particles is detected.

The contaminant particles on the surface of the wafer 9 will scatter the light beam 14 about each particle. The scattered light envelopes are then detected by the camera 11, and then sent to a processor 12, wherein a display is made of the particles.

In the preferred embodiment, the TV camera has a SIT(silicon intensified target) type of tube, which is highly sensitive to light and can detect light source not visible to the human eye. A camera which was used successfully is model C1000-12 manufactured by the Hamamatsu T.V. Co, Ltd. Another type camera which may be used is a two stage infrared channel plate type camera. The camera may be held stationary, and the lens 15 used to focus on different parts of the wafer 9 surface, with the light beam 14 impinging on the selected areas.

Figure 3:
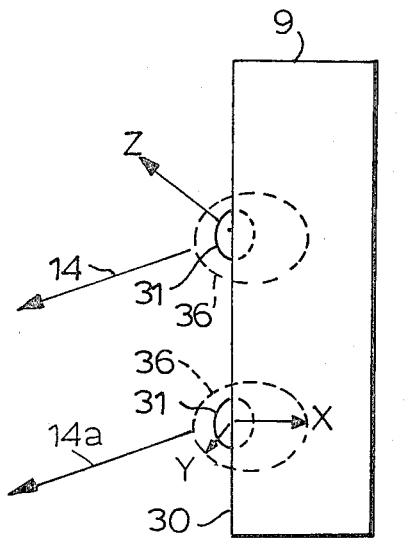
FIG. 3 depicts the mechanism of light scatter produced by the particles acting on the collimated light, and the reflection back of the collimated light from the wafer surface.

Turning now to FIG. 3, there is depicted a wafer 9 having a surface 30 on which particles 31 are disposed. These are contaminant particles incident on the wafer surface, e.g. remaining after an ordinary cleaning process and may be harmful to the later building of integrated circuits therefrom. They may range in size from 0.3 microns and larger. When collimated light beam 14 is directed onto the surface, the beam will hit the particles, such as beam 14a hits particle 31, and then be reflected back toward the collimating mirror 6 (see FIG. 2). The particles will cause light scattering, as shown by the envelope 36, which will be longer in the forward (i.e. right) direction designated "Y", than the back side direction "X". The scattered light, when viewed by the camera 11 from the direction "Z", will comprise parts of the front and back of the scattered light where the forward scatter is reflected off the wafer surface. The intensity of the scattered light will depend upon the size of the particle. Thus, the camera 11 will detect the scattered light, and by the intensity of the scattered light will be able to determine the size of the particle. The collimated light is not reflected specularly into the camera.

As above discussed, the iris 7 can be adjusted to limit the light beam on a specific area of the surface of wafer 9, and prevent light from reaching the edges of the wafer, for example. In an alternative embodiment, a mask 60 having an opaque, such as black material, surface may be placed on or near lens 2 of the light source 1. The mask (see FIG. 6) may have one or more holes 61 and can be moved by motor means 62 or manually by hand. In this manner, the light beam can be readily directed to specific areas of the wafer surface.

The camera 11 is provided with an appropriate lens 15 for suitably focusing on the wafer surface. By changing the magnificance, the field of view of lens 15 can comprise the entire surface or a small part thereof. When the field is restricted to a small area of the wafer surface, smaller sizes of particles can be more readily detected. Thus, for example, it is possible to detect 0.5 micron particles when viewing the entire surface of a 3 inch wafer, and to detect smaller than 0.5 micron particles, when viewing only one sector thereof. Theoretically, it is possible to detect particles of 0.1 microns using this invention. There have been seen, it is believed, particles of 0.3 microns using this invention.

Advantageously, this invention employs a light beam having a broad spectrum of wave lengths. For example, using a 150 watt Xenon arc lamp having a wavelength range of from 350 to 850 nanometers, the short wave length will best cause light scattering by the smaller particles. The longer wave lengths will best cause scattering by the larger particles. Other ranges of wavelengths are also utilizable. As a rule of thumb, the lower limit of the size of particles is one-half of the wavelength of the light used to illuminate the particles.

The intensity of the light from the scattering is indicative of the size of the particles. Thus, prior to measurement, a calibration procedure will be advantageously used. The scattered light from a particular particle is measured as to intensity and size and compared to the actual physical size of the particle using a microscope. Then, the light intensity of that size could be compared to the calibration. Background light in the different cases can be prevented by presetting the background intensity on the processor.

Figure 4:
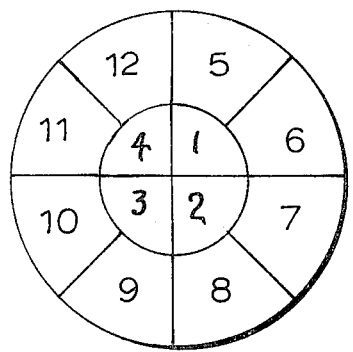
FIG. 4 depicts the sequential pattern of viewing of selected portions of the wafer surface.

Depending on the extent of the area of the surface being examined or the details desired, more than one portion may be examined in sequence in order to examine the entire surface. In FIG. 4, there is depicted a scheme for examining different areas in sequence until the entire area is inspected. For example, first, area 1 is exposed to the light beam and read by camera 11; then the wafer 9 is moved by means of holder 8 to have the area 2 exposed to the light beam and read by camera 11. The similarly, areas 3 . . . are sequentially exposed to the light beam and read by the camera until the entire surface area is inspected. Instead of wafer 9 being moved, the iris 7 can be moved to enable the light beam to be more specifically directed to selected areas. Also, the mask 60 may be used with appropriate cut out areas for exposure of light to the selected areas.

In the Example of FIG. 4, for areas 1,2,3,4, a pie shaped mask may be used to direct the light beams to those corresponding areas, and for areas 5,6,7,8,9,10,11,12, an arc shaped mask may be used. When the particular sub-areas are being illuminated, the areas about the areas being read should be sharply defined and blacked out so that there will be no extraneous reflections and scatter. A mask 60, such as shown in FIG. 6, may be used for this purpose.

Turning back to FIGS. 1 and 2., the mirror 6, which is used to collimate the light beam 14, may be of any suitable shape, such as concave, to appropriately direct the light beam from source 1 onto the surface of wafer 9 in collimated form. The mirrors, as well as lenses 2,15, should be substantially clean so that no scattered light will appear in the camera 11, caused by the contamination on the mirrors and lenses.

The wafer 9 is held against the holding surface of the vacuum holder 8, which is evacuated by vacuum pump 10. The holder may be moved by a motor means or other means 16 so as to expose different portions of the surface to illuminate by light beam 14.

The housing is preferably black on the inside and encloses the entire arrangement so that no extraneous light, reflections or scatter, will interfere with or produce erroneous readings, and so that contaminants from the outside atmosphere do not contaminate the wafer, equipment and optical devices. All of the equipment within the housing 5 may be preferably painted or coated black to optimize operation, except for the lenses 2, 15 and mirror 6.

The pin hole device 3 is used to precisely define a small source of light in the collimating system. Also, extraneous light and reflections are excluded from the beam path by the pin hole device 3. The light beam is desirably collimated so that straight substantially parallel beams will hit the wafer surface and be reflected back to the light source without being diverted toward the camera 11. Where there is any substantial amount of reflections and refractions of light at the wafer surface caused by surface contaminants, the reflected light will cause a snowy condition to appear on the screen. Any good collimating arrangement may be used. The preferred pin hole device, suitable lens on the light source and collimating mirror have been found to be satisfactory and workable.

In a typical arrangement, the lens 2 may be of f/1.2, 50 mm, disposed in front of the light source 1 and adjustable to focus the light on the pin hole. The pin hole 3 is placed at the image plane of the light source. The mirror 6 may be concave and have a focal length of 750 mm, and is used to collimate the light beams. The mirror 6 may be about 6 inches in diameter, and thus be able to illuminate wafers up to that size. The typical design aims for illumination of about 5 inches of mirror.

In operation, the equipment is first adjusted for optimal conditions. The light source 1 is turned on, and lens 2 is adjusted to place an image of the arc at the pin hole 3, and then mirror 6 is adjusted to collimate the light for optimal collimated light at wafer 9 surface. The wafer is positioned to optimally reflect substantially all of the collimated light back to the source. Substantially no light from the light source is reflected toward the camera 11. The iris 7 is adjusted to place the light beam on the wafer and cut off any light extending beyond the wafer area being illuminated and inspected. The lens 15 which may be of f/4 or larger, is adjusted to focus the camera 11 on an appropriate part of the surface of wafer 9.

The particle sizes may first be calibrated by comparing the actual size of a particle using a microscope, with the intensity of the scattered light on the surface of the wafer caused by the same particle. Using this calibration, the sizes of the particles on other wafer surfaces may be accurately determined. Also, it is then possible to eliminate from the count by the camera, particles which are of a certain size, and also background noise can be compensated for, using known display unit techniques.

After initial set up, a wafer is inspected by placing same on the vacuum chuck 8, and the light source 1 is turned on. Collimated light will then illuminate the surface of wafer 9, and any particles on the surface will scatter the light. The scattered light will then be observed by the camera 11, and will be shown on a display screen in real time.

The processor 12 may be provided with appropriate circuitry and computer programming to enable counting of the particles at different parts of the screen which corresponds to the different areas of the wafer surface being examined, isolation of the particles by sizes, identification of the particles, measuring of the particles, etc. The camera is set to detect light in the background. The light which indicates the presence of a contaminant particle is scattered light resulting from the illumination of the particles by the collimated light. The inventive system eliminates substantially all reflected light, extraneous light, and scattered light not resulting from the particles. Suitable threshold values can be pre-set into the processor to compensate for any extraneous and unavoidable light near the wafer surface.

Figure 5:
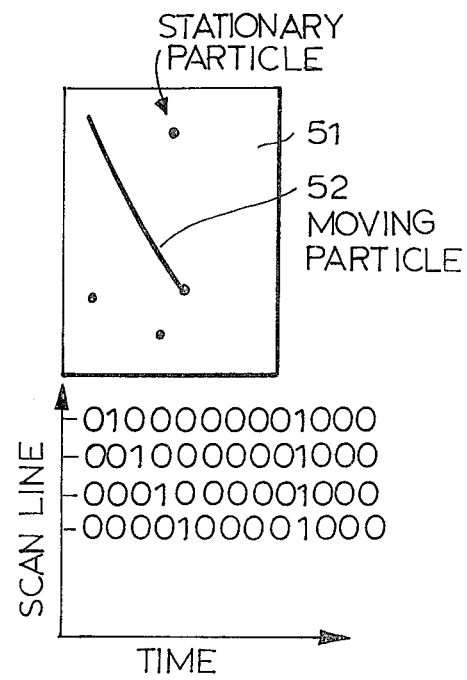
FIG. 5 depicts a graph showing the digital equivalent of the scanning of the surface against time, and superimposed upon the surface showing a moving particle.

Advantageously, the system of this invention enables the detection, identification, counting and measuring of the number and sizes of the particles on the surface of a wafer. In addition, advantageously, this invention enables the detection and identification of moving particles and to distinguish same from stationary particles. Turning now to FIG. 5, which is an illustration 51 of the wafer surface, there is depicted a moving particle which upon scanning by camera 11 is shown as curve 52. As the camera scans each horizontal line, the particle will be detected in a different location in the next line scan. Thus, for example, when converted to digital signals, such as appearing below the graph, the pattern of ones will show a different location, and thus, using appropriate circuitry and programming, the signals can be removed from the screen and other recording devices. Thus, the operator can see the movement of the particles on the screen, or he can remove same from the screen by actuating a circuit which upon detection of the moving pattern will remove such light from the screen. This feature is very important since even though a clean room is usually used when inspecting for contaminant particles, and laminar air flow is used, there is inevitably some moving contaminant particles in the area of the wafer inspection.

This invention is not limited to inspection of semiconductor wafers. It can be used in any situation wherein particles, scratches, or other imperfections or different materials need to be measured, detected, counted or located on a preferably, but not necessarily, reflective surface, e.g. optical mirrors, uniform metallic deposits, etc.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. A method of detecting contaminant particles on a material, comprising the steps of
   A. providing a substantially light reflectionless interior wherein detection is carried out;
   B. directing a collimated light beam onto a selected area of a surface of said material, whereby said particles will scatter light with intensities proportional to the sizes of said particles;
   C. adjusting the position of said surface to cause the collimated light to be reflected substantially back to the source without any substantial reflections or scatter;
   D. focusing a light sensitive TV camera on said surface of said material to detect the scattered light indicative of said particles; and
   E. processing signals received by said camera from said scattered light thereby to effect measurement, counting and determination of the location of said particles.

2. The method of claim 1, wherein said camera is of the silicon intensified target type.

3. The method of claim 1, wherein said collimated light beam is directed to an angle to said surface of said material and said camera is directed at an angle of up to 17° to said surface.

4. The method of claim 1, wherein the size of said contaminant particle detected by said camera is 0.3 micron and larger.

5. The method of claim 1, wherein prior to operation the sizes of said particles are calibrated by comparing the intensity of the scattered light corresponding to a particle to the actual physical size thereof as viewed and measured with a microscope.

6. The method of claim 1, wherein said material is a semiconductor wafer.

7. The method of claim 6, wherein said wafer is moved so that the surface of said wafer is illuminated in selected portions in succession until the desired surface area is completely inspected.

8. The method of claim 6 and wherein said collimated beam is blocked off over selected portions so as to illuminate only selected areas of said wafer.

9. The method of claim 1, wherein the light source has a range of wavelengths of from 3500 to 8500 Å.

10. The method of claim 1, wherein said light source is a Xenon or Hg-Xe arc lamp focused by a lens onto a pin hole, and then collimated by a concave collimating mirror.

11. A system for the detection of contaminant particles on or in a material, comprising
    A. a housing having interior walls of substantially light reflectionless material and substantially sealed to exclude external light;
    B. a source of light having a broad spectrum of wave lengths;
    C. an optimal system for collimating said light and directing the collimated light onto said material;
    D. means for movably holding said material to be inspected whereby said material is disposed to be exposed to impinging by said collimated light beams, and to have said collimated light beams strike said material and then be reflected back toward said source without any substantial reflection toward said camera, the particles causing light to be scattered,
    and wherein said optical system prevents reflection or scattering of said reflected light to interfere with the collimated light beam being directed at the material; and
    E. a light sensitive camera inside said housing positioned to view the said material whereby the scattered light indicative of the contaminant particles is detected by said camera.

12. The system of claim 11, wherein said housing comprises separate sections for the camera, the light source and the means for holding the material; and further having a laminar air flow device to keep the material being inspected substantially dust free.

13. The system of claim 11, wherein said optical system comprises a lens for focusing light from the light source onto
    a pin hole device for defining a small source and excluding extraneous light from the small source, a collimating mirror for collimating the light from the light source and to direct the collimated light beam onto the surface of said material; and means for defining the areas on which the collimated light beam will imping upon said material.

14. The system of claim 11, wherein the light source is a Xenon arc lamp having a wavelength range of from 3500 to 8500 Å.

15. The system of claim 11, wherein said TV camera is of the silicon intensified target type.

16. The system of claim 11, wherein said TV camera is of the two stage intensified channel plate type.

* * * * *